(12) United States Patent
Moschik (10) Patent No.: US 6,264,469 B1
(45) Date of Patent: Jul. 24, 2001

(54) ORTHODONTIC COMPONENT, IN PARTICULAR A BRACKET WITH AN INSERT ELEMENT

(75) Inventor: Erich Moschik, St. Veit/Glan (AT)

(73) Assignee: Advanced Products, Inc., Wilmington, NC (US)

( * ) Notice: Subject to any disclaimer, the term of this patent is extended or adjusted under 35 U.S.C. 154(b) by 0 days.

(21) Appl. No.: 09/452,996

(22) Filed: Dec. 2, 1999

(30) Foreign Application Priority Data

Dec. 10, 1998 (AT) .................................................. 2067/98

(51) Int. Cl.⁷ ...................................................... A61C 3/00
(52) U.S. Cl. ................................................... 433/8; 433/10
(58) Field of Search ................................... 433/8, 10, 16, 433/17

(56) References Cited

U.S. PATENT DOCUMENTS

| | | |
|---|---|---|
| 1,976,141 | 10/1934 | Richardson . |
| 2,045,025 | 6/1936 | Richardson . |
| 3,964,165 * | 6/1976 | Stahl .......................................... 433/8 |
| 4,249,897 * | 2/1981 | Anderson .................................. 433/8 |
| 4,299,569 * | 11/1981 | Frantz ....................................... 433/8 |
| 4,302,532 * | 11/1981 | Wallshein ................................. 438/8 |
| 4,322,206 | 3/1982 | Reynolds . |
| 4,430,061 | 2/1984 | Webb et al. . |
| 4,604,057 | 8/1986 | Viglietti . |
| 4,674,978 * | 6/1987 | Acevedo ................................... 433/8 |
| 4,952,141 * | 8/1990 | Wool ......................................... 433/8 |
| 4,954,080 | 9/1990 | Kelly et al. . |
| 5,078,596 * | 1/1992 | Carberry et al. ......................... 433/8 |
| 5,254,002 | 10/1993 | Reher et al. . |
| 5,358,402 * | 10/1994 | Reed et al. ............................... 433/8 |
| 5,380,196 * | 1/1995 | Kelly et al. .............................. 433/8 |
| 5,429,499 * | 7/1995 | Sernetz ..................................... 433/8 |
| 5,595,484 * | 1/1997 | Orikasa et al. .......................... 433/8 |
| 5,653,588 | 8/1997 | Moschik . |
| 5,813,852 * | 9/1998 | Kawaguchi ............................... 433/8 |
| 5,829,973 * | 11/1998 | Andreiko et al. ........................ 433/8 |

* cited by examiner

Primary Examiner—Nicholas D. Lucchesi
(74) Attorney, Agent, or Firm—Collard & Roe, P.C.

(57) ABSTRACT

The invention relates to an orthodontic component (1) with a base body (2) made from plastic (3), having a visible face (5), a base surface (6) spaced at a distance therefrom and side faces (7 to 10) extending between the latter. At least one slot-shaped recess (11) is arranged in the base body (2), which extends, starting from the visible face (5) in a direction towards the base surface (6) and between two oppositely lying side faces (7, 8). Arranged in the recess (11) is an insert element (4), which has a hardness value which is at most as high as the hardness value of the plastic (3) of the base body (2) of the component (1).

29 Claims, 3 Drawing Sheets

ORTHODONTIC COMPONENT, IN PARTICULAR A BRACKET WITH AN INSERT ELEMENT

BACKGROUND OF THE INVENTION

1. Field of the Invention

The invention relates to an orthodontic component with a base body made from plastic, having a visible face, a base surface spaced at a distance apart therefrom and side faces extending between the latter, at least one slot-shaped recess being arranged in the base body which extends starting from the visible face in a direction towards the base surface and between two oppositely lying side faces, and having an insert element arranged in the recess, as well as a method for its manufacture.

2. The Prior Art

A plastic orthodontic bracket is known from U.S. Pat. No. 5,254,002 A, which is made from a reinforced polycarbonate commonly used for plastic brackets. In order to strengthen it, at least 15% of fibres such as glass fibres, for example, are incorporated in this plastic material. Since the tooth alignment devices from which it is made are subjected to high mechanical stress, for example tensile forces, friction forces, etc. during chewing, and polycarbonate is not capable of withstanding these forces without sustaining damage when used for tooth alignment over a longer period of time, the groove of this tooth alignment device which is usually used to house the tensioning wire is provided with an extra reinforcing element which is stronger than the polycarbonate. The drawback of this is that the higher proportion of fillers used in the polycarbonate on the one hand and the metal reinforcement made of steel on the other have an adverse effect on the translucence and hence the overall appearance of the tooth alignment device. Furthermore, the friction forces transmitted from the tensioning wire to the bracket are not sufficiently reduced to prevent the bracket from suddenly being strained or breaking due to excessive strain, for example during chewing, because the tensioning wire is more easily able to slide off the internal surfaces of the groove in the bracket which receives the tensioning wire.

Another orthodontic component and a method for its manufacture is known from U.S. Pat. No. 5,653,588 A, the orthodontic component being made from a plastic material by an addition polymerisation which is terminated at a temperature corresponding at least to human body temperature. This is of particular importance to the selected plastic because no further changes of state can take place in the material of the bracket during use, particularly in the specific application for which it will be used. In order to strengthen the entire component, at least one reinforcement element can be arranged inside it, improving absorption and damping of the forces which occur during use, in particular pressure caused by chewing and the associated tensile and compression forces, without causing damage to the component. Furthermore, a friction-reducing element is arranged in the slot-shaped recess, which forms the side walls of the slot, at least in certain regions. This friction-reducing element is made from zircon oxide. The selected combination of the plastic and the friction-reducing element could only be used in quite specific applications as tooth attachments for tooth alignment devices.

In other known tooth alignment devices—disclosed in U.S. Pat. No. 1,976,141 A and U.S. Pat. No. 2,045,025 A—the tooth attachments are made from stainless steel and are secured to a stainless steel band which encircles the tooth in order to hold the tooth attachment in the appropriate position.

Various other tooth alignment methods and tooth alignment devices have been developed in which stainless steel tooth attachments are cemented directly onto the surface of the tooth. These methods and devices require no band to secure the tooth attachments. Such systems are often used. Tooth alignment methods and devices of this type are known amongst others from U.S. Pat. Nos. 4,604,057 A, 4,430,061 A and 4,322,206 A. The drawback of such stainless steel tooth attachments is their metallic appearance. Therefore, for reasons of appearance, adult patients in particular desire orthodontic devices which are not made of metal but of transparent or translucent materials, as such materials provide improved cosmetic appearance. Accordingly, transparent plastic materials are used, mostly polycarbonates or transparent or translucent ceramic materials made from aluminium oxide. In known tooth attachments consisting of non-metallic materials and produced in very small sizes to keep cosmetic drawbacks at a minimum, a known approach—disclosed in U.S. Pat. No. 4,302,532 A—is to increase the strength of ceramic tooth attachments made from plastic by using reinforcing elements.

Tooth alignment devices with a ceramic tooth attachment made from a polycrystalline ceramic structure with various additives are also known. One known ceramic tooth attachment—disclosed in U.S. Pat. No. 4,954,080 A—consists of polycrystalline ceramic having a light transmission in the visible spectrum, which reduces the visibility of this tooth attachment so that when it is mounted on the tooth, it can be hardly recognised by a third party. This polycrystalline ceramic body for the ceramic tooth attachment is produced by pressing powdered high purity aluminium oxide, which is then sintered to present a close to zero porosity and an average grain size in the range of 10 to 30 micrometers. Preferably, the tooth attachment should be colourless. An in-line light transmission in the visible spectrum should be 20% to 60% through a specimen having a thickness of 0.5 mm.

SUMMARY OF THE INVENTION

Accordingly, the underlying objective of the present invention is to provide an orthodontic component made from plastic, in which the friction forces which occur between the tensioning wire and the component due to sliding of the tensioning wire are reduced, and a method for its manufacture.

This objective of the invention is achieved in that the insert element has a hardness value which is at most equal to the hardness value of the plastic of the base body of the component. This design of an orthodontic component with the insert element inserted in the region of the slot is of advantage because the insert element has a lower hardness value than the plastic material of the base body. Accordingly, higher component strengths of the base body and hence longer residence times in orthodontic applications can be achieved without impairing relative movements between the tensioning wire or tautening wire and the region of the oppositely facing bearing surfaces of the orthodontic component. In view of the fact that the tensioning wire is pre-tensioned and because of its curved design, a free relative movement for adjustment would only be possible between the two parts due to the friction between them. Depending on the material used for the insert, a sort of lubricating effect is created between the latter and the tensioning wire, which is sufficient to reduce the friction forces between it and the tensioning wire.

An embodiment, where the orthodontic component is a bracket is also advantageous because the orthodontic component is designed in the form of a bracket already known from dental technology, which can be used specifically for re-aligning incorrectly aligned teeth.

Other embodiments, where the plastic of the base body has a hardness value of between 50 Shore D and 130 Shore D and/or between 80 Shore D and 100 Shore D, offer advantages since the hardness values selected for the base body allow the orthodontic component to be adapted to the most varied conditions of usage without having to take account of the sliding effect between the tensioning wire and the component, due to the two elements being interposed.

Due to the design and selection of the insert element in conjunction with the orthodontic component, the embodiments, in which the insert element is formed by a profile with a U-shaped cross section in a plane arranged perpendicular to its longitudinal extension and two arms spaced at a distance apart from one another, with surfaces running respectively on either side, as well as a cross-piece joining the two arms to one another in an end region, make it possible to adapt easily to cater for different applications. Further it is also useful, if the length of the insert element is shorter than a longitudinal extension of the slot-shaped recess and/or the length of the insert element corresponds to the longitudinal extension of the slot-shaped recess and/or the insert element has a varying width across its longitudinal extension transversely to the longitudinal extension.

Other individual advantages of further embodiments of the insert element will be explained in the detailed description.

Another embodiment, in which the insert element is made from an anti-allergenic, bio-compatible material and/or the material used for the insert element is selected from the group comprising gold (Au), silver (Ag), titanium (Ti), niobium (Ni), bismuth (Bi) and alloys of these elements has advantages because the entire component can be guaranteed to be compatible for the specific intended use.

Further embodiments are producing a better bonding capacity when the base surface of the component is subsequently cemented to the tooth of a patient.

Choosing a plastic material, where the plastic of the base body is a thermoplastic material or a highly cross-linked duroplastic material, both made by addition polymerisation terminated at a temperature corresponding at least to body temperature and/or the highly cross-linked duroplast is polyurethane, will ensure that there is no change in the state of the material during use, in particular in bodily orifices such as the mouth, for example. By using modern plastics, the hardness that can be produced in a bracket of this type can be likened to components made from aluminium oxide. Since the plastic is cross-linked, there is no subsequent change of the plastic material, which means that the user will not suffer any adverse effects due to the use of polyurethane and because polyurethane is also resistant to the aggression of various liquids which appear in the mouth, for example.

A particularly high-strength connection is achieved between the plastic of the base body and the insert element, when the plastic of the base body is moulded onto the insert element.

Further embodiments of the orthodontic components impart good optical properties to the orthodontic component, in particular translucence of the inherent colour of the tooth.

When the base surface of the base body is embedded with particles projecting out from at least certain regions of the plastic above the base surface and/or the particles in the base surface are silicon grains, silicon dioxide grains, ceramic grains, aluminium oxide grains (corundum grains), improved bonding properties of the orthodontic component on a tooth are produced.

Irrespective of the above, the objective of the invention can be achieved by means of a method of manufacturing an orthodontic component made from plastic and having an insert element. The advantages obtained, when the insert element is placed in a mould cavity of a mould before the plastic is introduced into the mould, where it is retained in position, and the plastic is then introduced into the cavity and hardened to form the orthodontic component, reside in the fact that the insert element is inserted in the mould cavity, where it is retained, before the plastic is introduced. As a result of this on-moulding procedure, a stable and strong connection can be produced between these two materials. In addition, this approach cuts out the subsequent process of placing the insert element in the slot region of the orthodontic component, which saves on costs and any layers of adhesive which might otherwise be needed.

A method, where the coating is tribo-chemically applied to the base surface and/or particles provided with a coating are accelerated and the base surface of the base body is then blasted with the accelerated particles and the coating on the particles melts during the blasting process due to the at least partial conversion of the kinetic energy imparted to the particles into thermal energy and the base surface of the base body is coated with a layer formed by the coating at least in certain regions, is advantageous because this additional coating process and the coating duly applied give the base surface a surface roughness so that indentations are produced in the base surface on the one hand as well as raised areas in the form of particles partially penetrating the base surface, formed during the coating process. This makes the subsequent process of connecting the requisite insert easier.

Other advantageous approaches, where the particles are added to the plastic before it is introduced in the mould cavity to form the orthodontic component and the particles are placed in the mould cavity of the mould before the plastic is introduced thereto, are also intended to make the subsequent process of cementing the orthodontic component onto a tooth easier and more secure.

BRIEF DESCRIPTION OF THE DRAWINGS

Examples of embodiments of the invention will be described in more detail in conjunction with the drawings, wherein.

DETAILED DESCRIPTION OF PREFERRED EMBODIMENTS

Firstly, it should be pointed out that in the various embodiments described, the same reference numbers and the same names are used to denote the same parts so that the same meaning can be ascribed to same parts with same reference numerals and same component names in the disclosures made throughout this description. Likewise, the terms used to denote positions throughout the description, e.g. top, bottom, side, etc., refer to the view of the drawing being described and can be transposed in terms of meaning to descriptions of different views. Furthermore, individual features or combinations of features relating to the different examples of embodiments described may also represent individual inventive solutions proposed by the invention in their own right.

Figure 1:
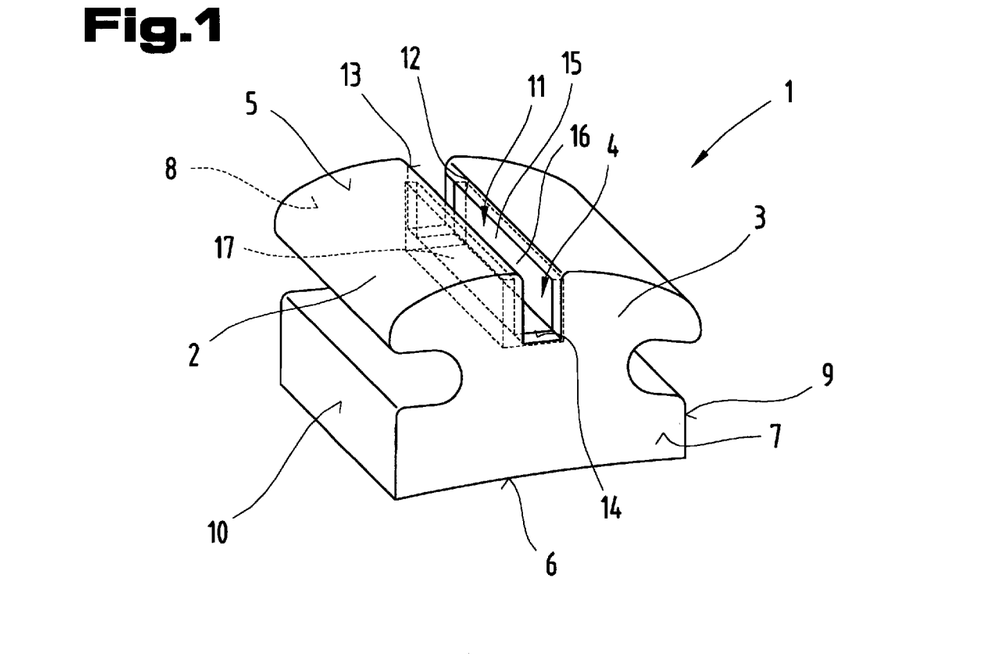
FIG. 1 is a simplified, schematic illustration, in perspective, of an orthodontic component as proposed by the invention, having an insert element.
Figure 2:
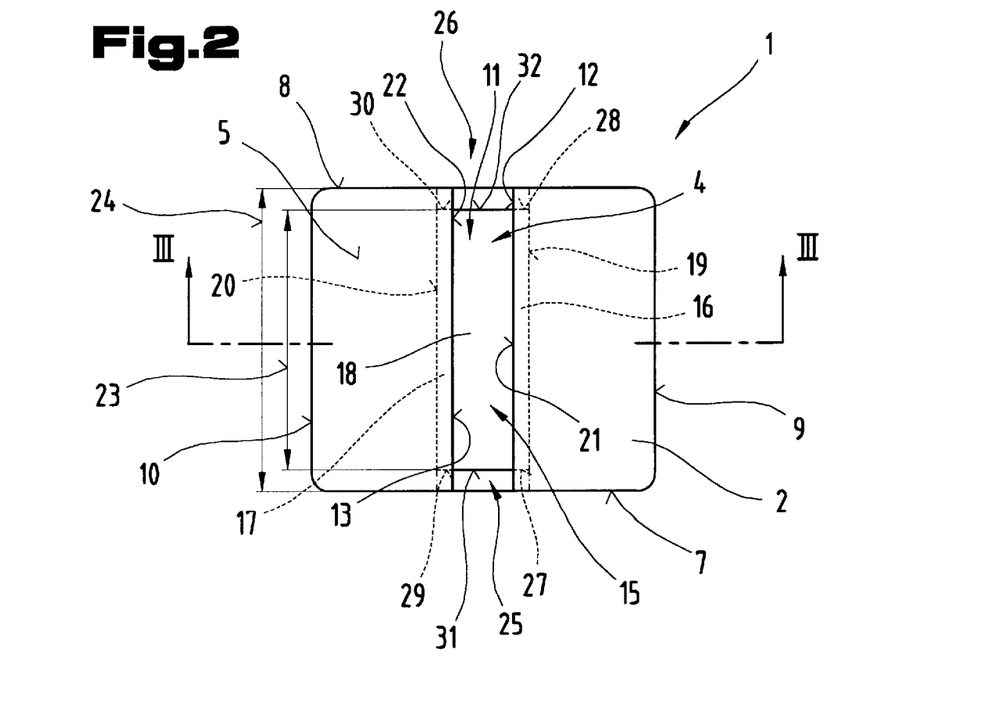
FIG. 2 is a plan view of the component illustrated in FIG. 1.
Figure 3:
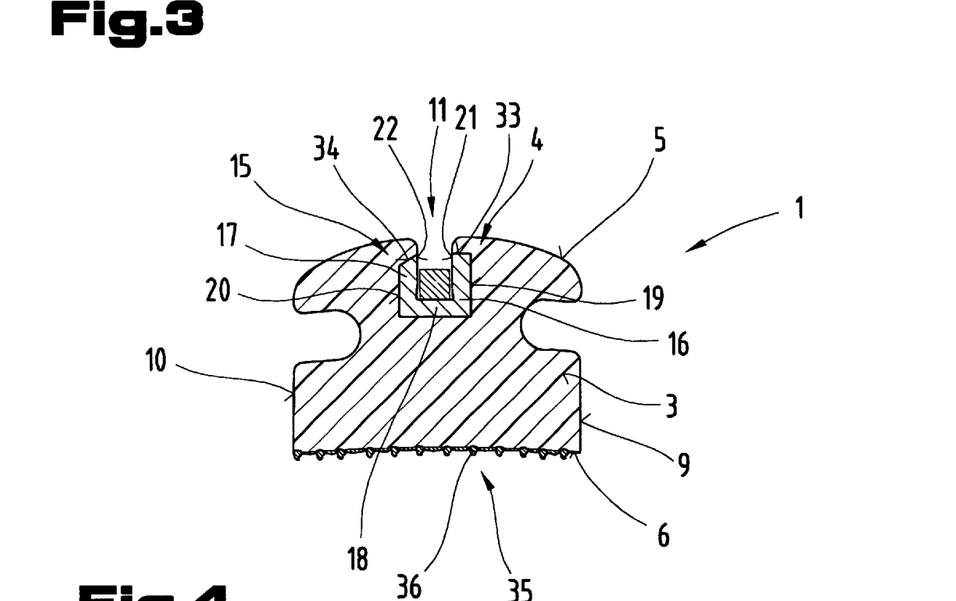
FIG. 3 illustrates the component of FIGS. 1 and 2 from a front view, along the lines III—III of FIG. 2.

FIGS. 1 to 3 illustrate an orthodontic component 1, in particular a bracket for adjusting incorrectly aligned teeth, which comprises a base body 2 made from a plastic 3 as well as an insert element 4.

The base body 2 of the orthodontic component 1 has a visible face 5, a base surface 6 spaced at a distance therefrom as well as side faces 7 to 10 extending between the latter, which determine the shape of the component 1. It should also be pointed out at this stage that the shape of the component 1 illustrated here is given by way of example only and is only one of many possible shapes, depending on the application for which it will be used. It should also be pointed out that the design of the base surface 6 and its shape may be very varied and the surface may be smooth or have groove-shaped recesses and the base surface may also have projecting raised areas which may also be of the most varied shapes.

The base body 2 also has at least one slot-shaped recess 11, which extends starting from the visible face 5 in a direction towards the base surface 6 and between the two oppositely lying side faces 7 and 8. This recess 11 is therefore arranged sunk into the component 1, starting from the visible face 5 in the base body 2, and preferably runs continuously between the two side faces 7 and 8.

The slot-shaped recess 11 also has side walls 12, 13 as well as a base wall 14 and its shape is also determined by these. In the example illustrated here, the slot-shaped recess 11 extends in a straight line between the two side faces 7, 8 but it could clearly also have a profile with a curved shape in its longitudinal extension or be inclined in its longitudinal extension relative to the two side faces 9 and 10.

As mentioned above, the insert element 4 is arranged in the region of the recess 11, so that the side walls 12, 13 and the base wall 14 are formed by the insert element 4 in some regions and by the plastic 3 of the base body 2 in some regions.

The casting compound used to make the base body 2 of plastic 3 is a casting resin in the form of a liquid dual-component substance, this casting resin having a base of a non-foaming urethane. Prior to determining their specific use, the two component elements of the casting resin are supplied in separate containers one of which will hold a main resin compound for the casting resin containing a binder with a polyol base and the other element, namely a hardener, having a base of diphenylmethane-4,4-diisocyante, for example. Accordingly, the plastic 3 of the component 1 may be a thermoplastic compound produced by an addition polymerisation terminated at a temperature corresponding at least to body temperature. Clearly, however, it would also be possible for the plastic 3 of the component 1 to be made from a highly cross-linked duroplastic compound, e.g. a polyurethane, in which case the addition polymerisation reaction would also be terminated at a temperature at least corresponding to body temperature. Consequently, the hardness values of the plastic 3 used will be between 50 Shore D and 130 Shore D, preferably between 80 Shore D and 100 Shore D, it being possible to select the hardness depending on the intended application. In view of the technical developments that have been made in the field of plastics 3, however, it would also be possible to select other, preferably higher hardness values for the plastic 3 than those given above. Irrespective of this, however, instead of using plastic 3 for the component 1, it would also be possible to use a polycrystalline aluminium oxide or zircon oxide, in which case the material used for the insert element 4 could be selected from those given below. The insert element 4 fulfils the exclusive role of a slide guide.

The orthodontic component 1 made from plastic 3 with its insert element 4 arranged therein can be made in such a way that, for example, the insert element 4 is placed in a mould cavity of a mould, that will not be described in more detail, before the plastic 3 or mixture used for this purpose is introduced into the mould cavity of the mould, where it will be retained in a predetermined position. The plastic 3 or mixture used to make it and form the base body 2 of the component 1 can then be introduced into the mould cavity and then hardened. Using this manufacturing technique, it would then be possible to mould the plastic 3 used to form the base body 2 of the component 1 onto the insert element 4, thereby joining it to the plastic 3 of the component 1. This joint may be a force fit or a positive fit. Alternatively, however, it would also be possible to join the insert element 4 to the plastic 3 of the base body 2 forming the component 1 by applying a layer of adhesive, at least in certain regions, coating the insert element 4 with a layer of adhesive or a primary coating in order to produce a better bond between the insert element 4 and the plastic 3.

As can be seen more clearly from FIGS. 2 and 3, the insert element 4 has a profile 15 having an approximately U-shaped cross section in a plane perpendicular to its longitudinal extension, as can be seen from the front view illustrated in FIG. 3. The profile 15 is formed by two arms 16, 17 arranged transversely to the longitudinal extension at a distance apart from one another and a cross-piece 18 joining the two arms 16, 17 to one another in an end region thereof. In their longitudinal extension, each of the two arms 16, 17 has external surfaces 19, 20 facing the base body 2 and internal surfaces 21, 22 which form the two side walls 12, 13 of the recess 11 in certain regions.

As may be seen more clearly from FIG. 2, the insert element 4 has a length 23 in a direction of the recess 11, which is shorter than a longitudinal extension 24 of the slot-shaped recess 11 extending between the two side faces 7 and 8. At respective opposing end regions 25, 26, the profile 15 of the insert element 4 also has end faces 27 to 30 bordering on the arms 16, 17 in a direction of the length 23. The cross-piece 18 also has an end face 31 in the end region 25 and another end face 32 in the end region 26. Due to the fact that the length 23 is selected to be shorter than the longitudinal extension 24, the individual end faces 27 to 32 of the insert element 4 are covered, at least in certain regions, by the plastic 3 of the base body 2 of the component 1. The entire insert element 4 is therefore retained inside the component 1 in such a way that it is prevented from being torn out.

As also illustrated by dotted-dashed lines in FIG. 2, it would also clearly be possible for the length 23 of the insert element 4 to be the same as the longitudinal extension 24 of the recess 11, in which case the end faces 27, 29 and 31 of the end region 25 would run more or less flush with the side face 7 of the component 1 and the end faces 28, 30 and 32 more or less flush with the side face 8. Clearly, however, it would also possible to arrange the individual end faces 27 to 32 at relative different distances from the side faces 7, 8 and/or flush with these.

As may be seen more clearly from FIG. 3, on the side remote from the cross-piece 18, the two arms 16, 17 have longitudinal side faces 33, 34 bordering the latter, at least one of these longitudinal side faces 33, 34 preferably being spaced at a distance from the visible face 5 of the base body 2. As illustrated here, both of the longitudinal side faces 33, 34 of the arms 16, 17 of the insert element 4 are arranged set back at a distance from the visible face 5 in a direction towards the base surface 6 of the base body 2. Since the longitudinal side faces 33, 34 are arranged set back at a distance from the visible face 5, they are covered by the plastic 3 of the component 1 in the region of the visible face 5, at least in certain regions.

As may also be seen in a simplified form from FIG. 3, the longitudinal side face 33 of the arm 16 is aligned substantially parallel with and perpendicular to the two surfaces 19, 21.

From the arm 17 illustrated on the left-hand side of FIG. 3, it can be seen that the longitudinal side face 34 is aligned at an angle to one of the two faces 20, 22 bordering the arm 17 but extends parallel with the two surfaces 20, 22. Clearly, however, it would also be possible for both longitudinal side faces 33, 34 to be inclined at a pre-determined angle to the respective surfaces 19, 21 and 20, 22 of the arms 16, 17. In a preferred embodiment, the two longitudinal side faces 33, 34 of both arms 16, 17 are designed so that they extend at a same opposing incline, in which case they will extend, starting from the two oppositely facing surfaces 21, 22 of the two arms 16, 17, in a direction towards the surfaces 19, 20 remote from one another, sloping in the direction of the cross-piece 18.

Designing the longitudinal side faces 33, 34 with a same opposing incline means that there will be no sharp-edged transition between the insert element 4 and the plastic 3 of the base body 2 in the overlap region with the longitudinal side faces 33, 34, thereby producing a strong and stable design for the bracket.

As may also be seen from the schematically simplified depiction of the base surface 6 region in FIG. 3, at least a part region of the base surface 6 of the component 1 is provided with a coating 35. This coating 35 is applied to the base surface 6 using a tribo-chemical coating process which induces and creates chemical bonding because of the mechanical energy applied. As illustrated in a very simplified manner, particles 36 may also be contained or embedded in this coating 35, these particles 36 being grains of silicon, grains of silicon dioxide, grains of ceramic, aluminium oxide grains (corundum grains), for example, in order to facilitate the subsequent process of bonding with a tooth surface, not illustrated, and improve the bonding properties of the entire component 1 in the region of the base surface 6 on the tooth surface. A more detailed description of the coating 35 as well as its component elements and how it works will be given in conjunction with one of the other drawings.

Figure 4:
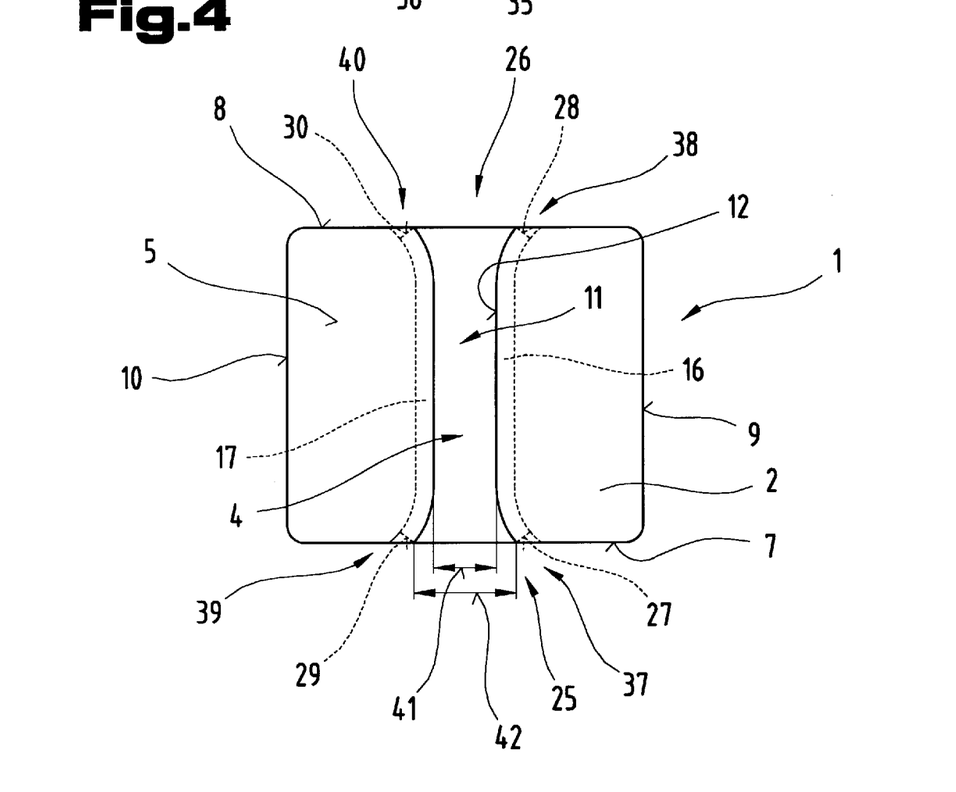
FIG. 4 is another and, as is the case, independent embodiment of the orthodontic component proposed by the invention with an insert element, seen from a plan view and illustrated in a simplified, schematic form.

FIG. 4 illustrates another embodiment of the component 1, in particular the insert element 4 in the base body 2, which can be regarded as an independent embodiment, the same reference numerals being used denote the elements common to those described in conjunction with FIGS. 1 to 3.

In this embodiment, the slot-shaped recess 11 also extends between oppositely lying side faces 7, 8 and is also aligned perpendicular to or at right angles to them. However, it would clearly also be possible to design the slot-shaped recess 11 between other side faces 9 and 10, also lying opposite one another, but each extending at an incline in the base body 2. In order to minimise friction between the tensioning wire or tautening wire, also known as a ligature wire, not illustrated, and the recess 11 of the component 1, at least one of the respective remote ends 37, 38 and 39, 40 of the arms 16, 17 can be so designed that it has a curved contour on the side remote from the slot-shaped recess 11, as schematically illustrated in simplified form. This being the case, the individual end faces 27, 28 and 29, 30 of the arms 16, 17 can be arranged at a distance from the side faces 7, 8 and/or substantially flush with them. Clearly, it would also be possible to arrange the individual end faces 27 to 30 at an angle to the side faces 7, 8. As a result of this curved contour of the ends 37 to 40, the recess 11, and the insert element 4 bordering it, has a differing width 41, 42 across its longitudinal extension and transversely to its longitudinal extension, the recess 11 becoming wider in the region of the side faces 7, 8.

Figure 5:
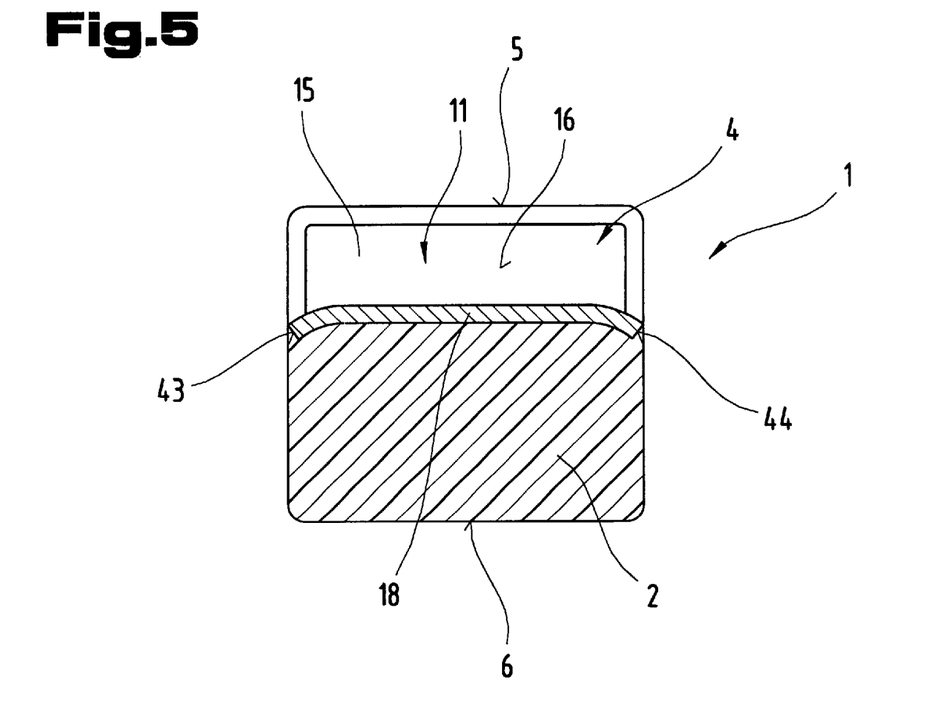
FIG. 5 is another and, as is the case, independent embodiment of the orthodontic component proposed by the invention with an insert element, seen from a front view and shown in a simplified, schematic form.

FIG. 5 illustrates another, also independent embodiment of the component 1, comprising the base body 2 and the insert element 4, which at least partially forms the slot-shaped recess 11, seen from a side view, the same reference numerals again being used to denote parts common to the previously described FIGS. 1 to 4.

The insert element 4 is again formed by the profile 15, only the arm 16 and the cross-piece 18 being shown in this instance. Again, in order to provide as friction-free a seat as possible for the tensioning wire, not illustrated, in the region of the cross-piece 18, ends 43, 44 of the cross-piece may have a curved contour, in a manner similar to that described in the context of the ends 37 to 40 of the arms 16 and 17 in FIG. 4. Preferably, the two ends 43, 44 of the cross-piece 18 are designed so that they extend on the side remote from the arms 16, 17 in a sloping curved design so that when the component 1 is used for its intended purpose, the tensioning wire will also extend along a curved longitudinal course within the recess 11, thereby preventing the tensioning wire from becoming misaligned in the region of the two ends 43, 44 when tautened or pulled from one end.

With all the insert elements 4 described above, the crucial factor is that they should have a lower friction coefficient than the plastic 3 used to make the base body 2 of the component 1. This will improve friction and improve the gliding properties between the tensioning wire and the insert element 4.

In order to improve compatibility for specific applications, the insert element 4 and/or the base body 2 forming the component 1 is made from an anti-allergenic, bio-compatible material. The materials which may be used to make the insert element 4 may be selected from gold (Au), silver (Ag), titanium (Ti), niobium (Nb), bismuth (Bi) and alloys of these elements, for example. If gold is used as the material, for example, it is of advantage to use gold alloys with different proportions of the noble metal. This applies above all to tooth gold. The crucial factor is that the insert element 4 should contain neither nickel (Ni) nor beryllium (Be).

In order to reduce visibility of the orthodontic component 1 when fitted on a tooth, it is of advantage if the plastic has an in-line translucence of between 5% and 90% for a thickness of 0.5 mm. This will ensure that the beams of light entering the orthodontic component 1 penetrate up to a tooth surface and are reflected by the latter, and a light beam corresponding to the colour of the tooth is reflected back by the component 1. Due to the fact that only a small proportion of the beams of light entering the component 1 are absorbed, the visual impression given is that the orthodontic component 1 takes on the colour of the tooth, which is the particular colouring of the teeth of user. Thus an orthodontic component 1 has been created in a simple manner, which on the one hand is easy to produce and on the other hand is optically very discreet for the user.

If the desired composition of the casting resin is to be changed accordingly, transmission of the light beams reflected back can be reduced or stopped. This causes the inherent colouring of the component 1 to come to the fore, producing a clear optical visibility with respect to the tooth.

The degree of radiation transmission of a material is defined by the degree of translucence, which is the ratio resulting from the intensity of the beam allowed to pass through and the intensity of the entering beam, with reference to radiation of a certain wavelength and a specimen of a certain thickness.

These variables are established by the following formula $$I/I_0 = ke^{-ad}$$

in which

"$I/I^0$" are the intensities of the beam passed through and of the incident beam;

"d" is the thickness of the specimen;

"a" is the absorption coefficient and

"k" is a constant which can be determined from the index of refraction of the material, which are expressed in relation to one another. In addition, the cone angle of the incident beam and the cone angle of the beam which has passed through must be specified.

The degree of transmission can be measured by means of a laser beam at a wave length of 0.63 mm so that the cone angle of the incident beam is close to zero. The cone angle of the beam which has passed through, which is used to determine the intensity of the transmitted beam, can be 60°, for example. This way, a transmission degree, i.e. an in-line translucence, can be defined.

Clearly, however, it would also be possible to measure this in-line translucence by means of a Perkin-Elmer-Lambda spectrophotometer, e.g. of the type 9UV/VIS/NIR, in which case the wavelength range may be between 400 nm and 800 nm.

Preferably, the thickness of the specimen is 0.5±0.005 mm, which means that a process of high quality surface finishing will be necessary, that is to say a very fine polishing, in order to avoid any of the light being reflected by irregularities on the surface of the specimen, which may change the measuring result to a great extent. Basically, it should be taken into account that measuring the in-line translucence is a difficult problem since the quantity of light used to expose the specimen to radiation is expressed in relation to the quantity of light of a given wavelength emerging from the specimen. The difference in these two light quantities lies in the fact that the irradiated light is deflected due to irregularities in the specimen, such as grains, grain boundaries and the like, and is therefore dispersed. This deflection and dispersion essentially depends on the size and the shape of the irregularities and measuring the light distribution becomes difficult if its size falls within the region of the wavelength that was used for this measuring test. Therefore, each test sample has to be produced with two surfaces that are plane-parallel with each other, which have to be polished to a predefined surface roughness.

To measure the in-line translucence, the test sample is exposed to a directed or parallel concentrated beam of light with little beam spread, which is oriented perpendicular to the surface of the test sample. A partial loss of the radiation intensity is caused by the transition of the radiation from the air onto the test sample due to the differing refractive index between the air and the test sample. The light intensity entering the test sample is then deflected in different directions by irregularities. Therefore, the permitted angle of incidence of the radiation with respect to the measuring device is an essential factor in determining the in-line translucence. The greater the permitted angle of incidence on the measuring device, the greater is the measured in-line translucence for the same test sample.

This is why for all testing, the angle of incidence of light from the light beam falling onto the test sample and also the angle of emergence of light of the emerging beam of light must be identical.

Preferably, an angle of 3° can be accepted as an angle of incidence, for example. This being the case, it is advantageous to use a beam directed onto the test sample which has a width of 0.2 mm and a height of 0.5 mm and to provide a screen with a diameter of 1 mm or respectively 0.5 mm.

However, it is also possible to set the angle of incidence of the beam to be let through at approximately 60°.

Essentially, in optical terms, the bracket assumes a colour corresponding to the colour of the tooth situated underneath if translucence is very high, for example between 70% and 90%, since the majority of the in-line transmittance of the light will then arrive vertically on the tooth and be reflected by the latter towards the outside so that an observer will essentially recognise only the colour of the tooth whilst the orthodontic component or the bracket appears to take on the colour of the tooth.

In the case of components which are very small relative to objects located behind them the colour of which they are intended to assume, it may be that an in-line translucence of 60%–80% or 30%–70% will suffice, since a greater proportion of the light reflected on different sides, and not in a straight direction, can also be reflected back, thereby causing the additionally mounted component to assume predominantly the colour of the background, making it almost invisible.

Lower translucence values of 5% to 30%, for example, can be used to impart to components of this type an inherent colour such, for example, that it is the proportion of colour inherent in the components that will predominate in the eyes of the observer. Due to the small amount of light reflected by the background, the effect of the underlying surface will be very slight, or will be sufficient, if the bracket is appropriately coloured to suit the base material, to balance nuances of colour if needed.

In components which are approximately adapted to the colour of the background, a better result is achieved if the in-line translucence is between 10% and 35%. This produces a good match between the colouring of a component and a proportion of the colour of the base body.

In order to improve the bonding properties or to improve the process of cementing the base surface 6 of the component 1 to a tooth, not illustrated, particles 36 may be embedded in regions of the plastic 3, protruding out from the base surface 6 and, as mentioned above, these particles may be provided in the form of silicon dioxide grains, ceramic grains, aluminium oxide grains (corundum grains) etc. The particles 36 can be arranged in the region of the base surface 6 by placing them in the mould cavity of the mould before the plastic 3 is introduced, for example. However, it would also be possible to add these particles 36 to the plastic 3 before introducing it into the mould cavity used to form the orthodontic component 1.

Figure 6:
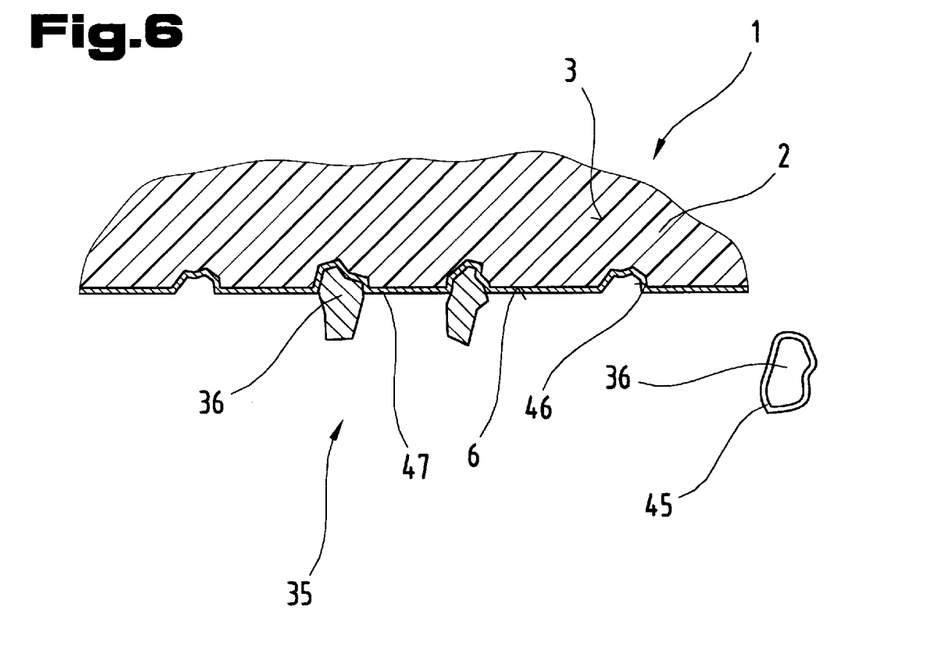
FIG. 6 is a part region of the base surface of the component from a front view and in an enlarged, simplified schematic form, illustrating the coating applied.

FIG. 6 depicts a part region of the base surface 6 of the orthodontic component 1 in section from a front view and in an enlarged, schematic illustration, in order to provide a clear idea of the coating 35 applied to it and the coating process. For the sake of avoiding unnecessary repetition, the same reference numerals will be used for parts common to the previously described FIGS. 1 to 5. It should be pointed out that this coating process by which the coating 35 is applied is not restricted to the component 1 with the insert element 4 described above but can clearly be used for any orthodontic components 1, in particular for brackets made from the most varied of plastic materials.

The base body 2 of the component 1 may be made from the types of plastic 3 mentioned above, the drawing giving a simplified illustration of the coating 35 applied to the base surface 6 thereof. This drawing shows the coating 35 already applied and this may also incorporate the particles 36 or grains mentioned above, which may be of the most varied materials such as silicon, silicon dioxide, ceramic, aluminium oxide (corundum), etc., for example. If these aforementioned materials are used, they should be of a predetermined grain size of 110 mm, for example, and they are provided with a coating 45 at least in certain regions. This coating 45 is mostly made from a silicate, which is applied to the individual particles 36 in a certain coating thickness. These particles 36 with the coating 45 are accelerated by means of an air flow, for example, and are displaced in the direction of the base surface 6 in a sand-blasting process so that a kinetic energy is imparted to the particles. In view of the high speeds prevailing during the application process, the particles 36 hit the base surface 6 of the base body 2 and penetrate the base surface 6, at least partially, thereby forming small indentations 46. These indentations 46 may be regarded as micropores.

As the particles 36 with the coating 45 are blasted, they partially penetrate the base surface 6 of the base body 2 as described above on the one hand and, in addition, due to the partial conversion of the kinetic energy as they collide with the moulding work and the heat, the coating 45 melts, running off the particles 36 in this state onto the base surface 6 of the base body 2, where they form a layer 47. The thickness of the layer 47 will depend on the level of coating by the particles 36 and on the duration of the process by which they are applied to the base surface 6. As a result of the high-impact energy of the particles 36 on the base surface 6, a tribo-chemical coating is applied to the base body 2 so that chemical bonds are produced due to the kinetic energy applied. As the base surface 6 of the base body 2 is blasted with the accelerated particles 36, the coating 45 of the particles 36 is melted during the blasting process, due to the at least partial conversion of the kinetic energy imparted to the particles 36 into thermal energy, and the base surface 6 of the base body 2 is coated with the layer 47 produced by the coating 45, at least in certain regions.

As a result of the high-impact energy of the individual particles 36, the coating 45 also melts in the region of the indentation 46 so that a layer 47 is also formed in this region. The impact energy and the associated melting process of the coating 45 cause some of the particles 36 to be retained on the base surface 6, whilst a certain proportion thereof is blasted back off due to subsequent ablation, deformation and a build-up of heat and only the layer 47 formed by the coating 45 remains on the base surface 6 of the base body 2. Depending on the plastic 3 used for the base body 2, a proportion of between 5% and 90%, preferably between 40% and 70% of the particles 36 will remain on the base surface 6, whilst the rest is 100% blasted off the base surface 6 and does not produce an adhesion bond.

Applying or coating the base surface 6 with the particles 36 increases the surface roughness in the form of indentations 46 and particles 36 projecting out from the base surface 6. This produces a better adhesive effect between the component 1 and the surface of a tooth when used in specific applications mounted on a tooth or its surface, not illustrated here.

The coating 45 forming the layer 47 may also be formed by silicon or a silicon compound, which will also melt due to the kinetic energy applied during blasting, being transferred to the base surface 6. The effect of the impact simultaneously causes a certain amount of ablation or deformation on the base surface 6 and applies the coating 35 to the base surface 6 from the coating 45. After the layer 47 has been formed by the coating 45, which may be distributed at least in certain regions across the base surface 6 of the base body 2, no further treatment or coating of the base surface 6 of the base body 2 is generally necessary.

The coating 35 and the particles contained therein 36 can be applied to the base surface 6 with compressed air in a process of the sand-blasting type.

For the sake of good order, it should be pointed out that in order to provide a clearer understanding of the structure of the orthodontic component 1, it and its components are not illustrated to scale and/or are on an enlarged and/or a reduced scale.

The task underlying the independent solutions proposed by the invention can be taken from the description.

Above all, the individual embodiments illustrated in FIGS. 1, 2, 3; 4; 5; 6 may be regarded as the object of independent solutions proposed by the invention. The tasks and solutions proposed by the invention can be taken from the detailed descriptions given with reference to these drawings.

LIST OF REFERENCE NUMBERS

1 Component
2 Base body
3 Plastic
4 Insert element
5 Visible face
6 Base surface
7 Side face
8 Side face
9 Side face
10 Side face
11 Recess
12 Side wall
13 Side wall
14 Base wall
15 Profile
16 Arm
17 Arm
18 Cross-piece
19 Surface
20 Surface
21 Surface
22 Surface
23 Length
24 Longitudinal extension
25 End region
26 End region
27 End face 28 End face
29 End face
30 End face
31 End face
32 End face
33 Longitudinal side face
34 Longitudinal side face
35 Coating
36 Particle
37 End
38 End
39 End
40 End
41 Width
42 Width
43 End
44 End
45 Coating
46 Indentation
47 Layer

What is claimed is:

1. An orthodontic bracket comprising
   (a) a base body made from plastic, the plastic being a highly cross-linked polyurethane made by addition polymerization terminated at a temperature corresponding at least to body temperature, and the base body having
      (1) a visible face,
      (2) a base surface spaced therefrom,
      (3) side faces extending between the visible face and the base surface, and
      (4) at least one slot-shaped recess extending between two oppositely lying side faces from the visible face towards the base surface,
   (b) an insert element arranged in the recess, the insert element having a hardness value which is at most equal to the hardness value of the plastic of the base body and a lower friction coefficient than the plastic of the base body,
      (1) the plastic base body being molded onto the insert element, and
   (c) a coating containing particles applied to at least some regions of the base surface.

2. Orthodontic bracket according to claim 1, characterised in that the plastic of the base body has a hardness value of between 50 Shore D and 130 Shore D.

3. Orthodontic bracket according to claim 2, characterised in that the plastic of the base body has a hardness value of between 80 Shore D and 100 Shore D.

4. Orthodontic bracket according to claim 1, characterised in that the insert element is formed by a profile with a U-shaped cross section in a plane arranged perpendicular to its longitudinal extension and two arms spaced at a distance apart from one another, with surfaces running respectively on either side, as well as a cross-piece joining the two arms to one another in an end region.

5. Orthodontic bracket according to claim 1, characterised in that a length of the insert element is shorter than a longitudinal extension of the slot-shaped recess.

6. Orthodontic bracket according to claim 1, characterised in that the length of the insert element corresponds to the longitudinal extension of the slot-shaped recess.

7. Orthodontic bracket according to claim 1, characterised in that the insert element has a varying width across its longitudinal extension transversely to the longitudinal extension.

8. Orthodontic bracket according to claim 1, characterised in that at least one of the longitudinal side faces of a arm of the insert element facing the visible face is arranged set back at a distance from the visible face.

9. Orthodontic bracket according to claim 1, characterised in that at least one of the longitudinal side faces of a arm of the insert element facing the visible face is arranged at a distance from the visible face in a direction towards the base surface.

10. Orthodontic bracket according to claim 1, characterised in that at least one of the longitudinal side faces of the insert element is covered by the plastic of the base body, at least in certain regions.

11. Orthodontic bracket according to claim 1, characterised in that at least one of the longitudinal side faces of the insert element is arranged at an angle to one of the two surfaces bordering the arms.

12. Orthodontic bracket according to claim 1, characterised in that the longitudinal side faces of the two arms of the insert element are designed so as to extend at a same opposing angle.

13. Orthodontic bracket according to claim 1, characterised in that the longitudinal side faces of the insert element are designed to extend, starting from the two oppositely facing surfaces of the arms, in a direction towards the surfaces remote from one another, sloping in the direction of the cross-piece.

14. Orthodontic bracket according to claim 1, characterised in that at least one of the ends of the cross-piece of the insert element remote from one another extends in a curved shape to the side remote from the arms.

15. Orthodontic bracket according to claim 1, characterised in that at least one of the ends of at least one arm of the insert element remote from one another extends in a curved shape to the side remote from the slot-shaped recess.

16. Orthodontic bracket according to claim 1, characterised in that the end faces of the insert element formed by the profile bordering the latter in the longitudinal extension thereof is covered, at least in certain regions, by the plastic of the base body.

17. Orthodontic bracket according to claim 1, characterised in that the insert element is made from an anti-allergenic, bio-compatible material.

18. Orthodontic bracket according to claim 1, characterised in that the material used for the insert element (4) is selected from the group comprising gold (Au), silver (Ag), titanium (Ti), niobium (Ni), bismuth (Bi) and alloys of these elements.

19. Orthodontic bracket according to claim 1, characterised in that the particles in the coating are silicon grains, silicon dioxide grains, ceramic grains, aluminium oxide grains (corundum grains).

20. Orthodontic bracket according to claim 1, characterised in that the particles are provided with a coating which forms a layer, at least in certain regions.

21. Orthodontic bracket according to claim 1, characterised in that the material used for the coating is a silicate, a silicon or a silicon compound.

22. Orthodontic bracket according to claim 1, characterised in that the proportion of particles which remains on the base surface of the base body is between 5% and 90%, preferably between 40% and 70%.

23. Orthodontic bracket according to claim 1, characterised in that the plastic of the base body has an in-line translucence of between 5% and 90% for a thickness of 0.5 mm.

24. Orthodontic bracket according to claim 1, characterised in that the plastic of the base body has an in-line translucence of between 70% and 90% for a thickness of 0.5 mm.

25. Orthodontic bracket according to claim 1, characterised in that the plastic of the base body has an in-line translucence of between 60% and 80% for a thickness of 0.5 mm.

26. Orthodontic bracket according to claim 1, characterised in that the plastic of the base body has an in-line translucence of between 30% and 70% for a thickness of 0.5 mm.

27. Orthodontic bracket according to claim 1, characterised in that the plastic of the base body has an in-line translucence of between 5% and 30% for a thickness of 0.5 mm.

28. Orthodontic bracket according to claim 1, characterised in that the base surface of the base body is embedded with particles projecting out from at least certain regions of the plastic above the base surface.

29. Orthodontic bracket according to claim 1, characterised in that the particles in the base surface are silicon grains, silicon dioxide grains, ceramic grains, aluminium oxide grains (corundum grains).

* * * * *